United States Patent
Datta et al.

(10) Patent No.: US 11,382,364 B2
(45) Date of Patent: Jul. 12, 2022

(54) WEARABLE HEALTH MONITORING FABRIC

(71) Applicant: HEMODYNAMIQ WEARABLES PRIVATE LIMITED, Bangalore (IN)

(72) Inventors: Deepanjan Datta, Kolkata (IN); Ratnadipa Banerjee, Kolkata (IN); Sai Kamalesh, Bangalore (IN)

(73) Assignee: HEMODYNAMIQ WEARABLES PRIVATE LIMITED, Bangalore (IN)

( * ) Notice: Subject to any disclaimer, the term of this patent is extended or adjusted under 35 U.S.C. 154(b) by 106 days.

(21) Appl. No.: 16/105,196

(22) Filed: Aug. 20, 2018

(65) Prior Publication Data

US 2019/0373962 A1    Dec. 12, 2019

(30) Foreign Application Priority Data

Jun. 8, 2018    (IN) .............................. 201831021669

(51) Int. Cl.
*A41D 1/04*    (2006.01)
*A41D 1/00*    (2018.01)
(Continued)

(52) U.S. Cl.
CPC ................ *A41D 1/002* (2013.01); *A41B 1/00* (2013.01); *A41C 3/0064* (2013.01); *A41D 1/02* (2013.01);
(Continued)

(58) Field of Classification Search
CPC ......... A61B 5/02; A61B 5/025; A61B 5/0255; A61B 5/021; A61B 5/0253; A61B 5/108;
(Continued)

(56) References Cited

U.S. PATENT DOCUMENTS

| | | | |
|---|---|---|---|
| 7,559,902 B2 * | 7/2009 | Ting ..................... | A61B 5/0408 600/529 |
| 9,414,758 B1 * | 8/2016 | Brockway ............ | A61B 5/6804 |

(Continued)

FOREIGN PATENT DOCUMENTS

| | | |
|---|---|---|
| WO | 2005027720 A2 | 3/2005 |
| WO | 2015056262 A1 | 4/2015 |
| WO | 2017198891 A1 | 11/2017 |

OTHER PUBLICATIONS

Seoane et al., "Sensorized Garments and Textrode-Enabled Measurement Instrumentation for Ambulatory Assessment of the Autonomic Nervous System Response in the ATREC Project," Sensors 2013, 13, 8997-9015.*

(Continued)

*Primary Examiner* — Ahmed M Farah
(74) *Attorney, Agent, or Firm* — Horizon IP Pte Ltd.

(57) ABSTRACT

A wearable health monitoring fabric is provided. The wearable fabric includes a set of textrodes. The set of textrodes is configured to measure thoracic electrical bioimpedance (TEB) of a user's body. The set of textrodes include at least two first textrodes. The set of textrodes also include at least two second textrodes. The set of textrodes is fabricated on an upper part of the wearable fabric. Further, the wearable health monitoring fabric is more compatible and user friendly as the textrodes are non-invasive in nature.

8 Claims, 9 Drawing Sheets

(51) Int. Cl.
| | |
|---|---|
| *A41B 1/00* | (2006.01) |
| *A41D 1/02* | (2006.01) |
| *A61B 5/0205* | (2006.01) |
| *A41C 3/00* | (2006.01) |
| *A61B 5/00* | (2006.01) |
| *A61B 5/021* | (2006.01) |
| *A61B 5/024* | (2006.01) |
| *A61B 5/053* | (2021.01) |
| *A61B 5/08* | (2006.01) |
| *A61B 5/145* | (2006.01) |
| *A61B 5/282* | (2021.01) |

(52) U.S. Cl.
CPC ............ *A41D 1/04* (2013.01); *A61B 5/02055* (2013.01); *A61B 5/6805* (2013.01); *A61B 5/021* (2013.01); *A61B 5/02416* (2013.01); *A61B 5/053* (2013.01); *A61B 5/0816* (2013.01); *A61B 5/14542* (2013.01); *A61B 5/282* (2021.01); *A61B 2562/0215* (2017.08); *A61B 2562/0219* (2013.01)

(58) Field of Classification Search
CPC ..... A61B 5/10816; A61B 5/68; A61B 5/6801; A61B 5/6802; A61B 5/6804; A61B 5/6805; A61B 5/6823; A61B 5/0205; A61B 5/02055; A61B 5/05; A61B 5/053; A61B 5/08; A61B 5/0816; A61B 5/28; A61B 5/282; A41D 1/00; A41D 1/002; A41D 1/005; A41D 1/02; A41D 1/04; A41D 1/008; A41D 1/14; A41D 1/18
USPC ................ 600/301, 372, 382, 386, 388, 389
See application file for complete search history.

(56) References Cited

U.S. PATENT DOCUMENTS

| | | | |
|---|---|---|---|
| 9,986,771 B2* | 6/2018 | Longinotti-Buitoni | A61B 5/6805 |
| 10,548,511 B2* | 2/2020 | Kruger | G06F 3/0346 |
| 2005/0054941 A1* | 3/2005 | Ting | A61B 5/6804 600/529 |
| 2005/0059896 A1* | 3/2005 | Drakulic | A61B 5/04085 600/509 |
| 2006/0135863 A1* | 6/2006 | Birnbaum | A61B 5/0002 600/388 |
| 2011/0060215 A1 | 3/2011 | Tupin, Jr. et al. | |
| 2012/0136231 A1* | 5/2012 | Markel | A41D 19/0027 600/388 |
| 2016/0029953 A1* | 2/2016 | Bonomi | A61B 5/4875 600/529 |
| 2016/0183835 A1* | 6/2016 | Varadan | A61B 5/08 600/484 |
| 2016/0296114 A1* | 10/2016 | Finch | A61B 5/0404 |
| 2017/0172516 A1* | 6/2017 | Banet | G16H 40/67 |
| 2017/0224280 A1* | 8/2017 | Bozkurt | G01L 5/0014 |
| 2017/0281462 A1* | 10/2017 | Freeman | A61B 5/6805 |
| 2017/0354372 A1* | 12/2017 | Varadan | A61B 5/282 |
| 2018/0311530 A1* | 11/2018 | Kruger | G06F 3/015 |
| 2019/0298987 A1* | 10/2019 | Freeman | A61B 5/6823 |
| 2020/0008299 A1* | 1/2020 | Tran | A61B 5/686 |

OTHER PUBLICATIONS

Marquez et al., "Textrode-enabled transthoracic electrical bioimpedance measurements—towards wearable applications of impedance cardiography," </i> J Electical Bioimp, vol. 4, pp. 45-50, 2013.*

* cited by examiner

WEARABLE HEALTH MONITORING FABRIC

FIELD OF INVENTION

Embodiments of the present disclosure relate to health monitoring of a user and more particularly to a wearable health monitoring fabric.

BACKGROUND

Chronic health failure and associated trauma are a major health concern worldwide. Heart failure, stroke, and high blood pressure are common cardiovascular and cardiopulmonary problems which are increasing in both prevalence and incidence and associated with substantial morbidity and mortality. The impact of cardiovascular diseases (CVDs) is felt not only in reduced health, but also in lower productivity. The increasing number of premature deaths caused by CVDs is causing great loss to families. Thus, requires proper prediction of such diseases at early stages so that the diseases can be monitored and diagnosed correctly and thereby prevented.

One such type of health monitoring system for monitoring heart functioning of a user includes a wearable device, provided with various electrodes, which is placed on a user's body from where electrical pulses of the heart is to be measured. Further, the electrodes are invasive in nature. Hence, such invasive electrodes are painful and at times causes infection to the user's body if the electrodes are not well sterilized, thereby making the wearable device incompatible for the user. Also, such invasive electrodes are limited to measure various parameters of heart functioning. Henceforth several such wearable devices have to be coupled to the user's body to measure different parameters.

Another type of health monitoring system includes a wearable garment having several electrodes along with a plurality of sensors deployed along the wearable garment, where the electrodes are configured to measure several parameters of a user's body such as blood pressure, heart rate, blood sugar level, lactate level and oxygen saturation level or the like. Moreover, the electrodes along with the plurality of sensors are to be fastened to the user's body through some adhesives to measure the parameters from the user's body. Further, several users may develop an allergic nature towards such adhesives which leads to numerous other complications. Also, due to the involvement of the adhesives, the parameters to be measured are intervened by noise. Hence, the efficiency of the system is reduced.

Hence, there is a need for an improved wearable health monitoring fabric to address the aforementioned issues.

BRIEF DESCRIPTION

In accordance with one embodiment of the disclosure, a wearable health monitoring fabric is provided. The wearable fabric includes a set of textrodes configured to measure thoracic electrical bioimpedance (TEB) of a user's body. The set of textrodes include at least two first textrodes. The set of textrodes also includes at least two second textrodes. The set of textrodes is fabricated on an upper part of the wearable fabric.

In accordance with another embodiment of the disclosure, the wearable health monitoring fabric further includes a computing device operatively coupled to the wearable fabric. The computing device is configured to obtain and process a measured thoracic electrical bioimpedance (TEB).

In accordance with another embodiment of the disclosure, the wearable health monitoring fabric further includes one or more sensors operatively coupled to one or more textrodes. The one or more sensors are configured to sense one or more physiological signals generated by the user's body.

In accordance with yet another embodiment of the disclosure, the wearable health monitoring fabric further includes a computing device operatively coupled to the wearable fabric. The computing device is configured to obtain and process the one or more physiological signals sensed by the corresponding one or more sensors.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF THE DRAWINGS

The disclosure will be described and explained with additional specificity and detail with the accompanying figures in which.

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the an are to be construed as being within the scope of the present disclosure.

The terms "comprises", "comprising", or any other variations thereof, are intended to cover a non-exclusive inclusion, such that a process or method that comprises a list of steps does not include only those steps but may include other steps not expressly listed or inherent to such a process or method. Similarly, one or more devices or sub-systems or elements or structures or components preceded by "comprises . . . a" does not, without more constraints, preclude the existence of other devices, sub-systems, elements, structures, components, additional devices, additional sub-systems, additional elements, additional structures or additional components. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

In the following specification and the claims, reference will be made to a number of terms, which shall be defined to have the following meanings. The singular forms "a", "an", and "the" include plural references unless the context clearly dictates otherwise.

Embodiments of the present disclosure relate to a wearable health monitoring fabric is provided. The wearable fabric includes a set of textrodes. The set of textrodes is configured to measure thoracic electrical bioimpedance (TEB) of a user's body. The set of textrodes include at least two first textrodes. The set of textrodes also include at least two second textrodes. The set of textrodes is fabricated on an upper part of the wearable fabric.

Figure 1:
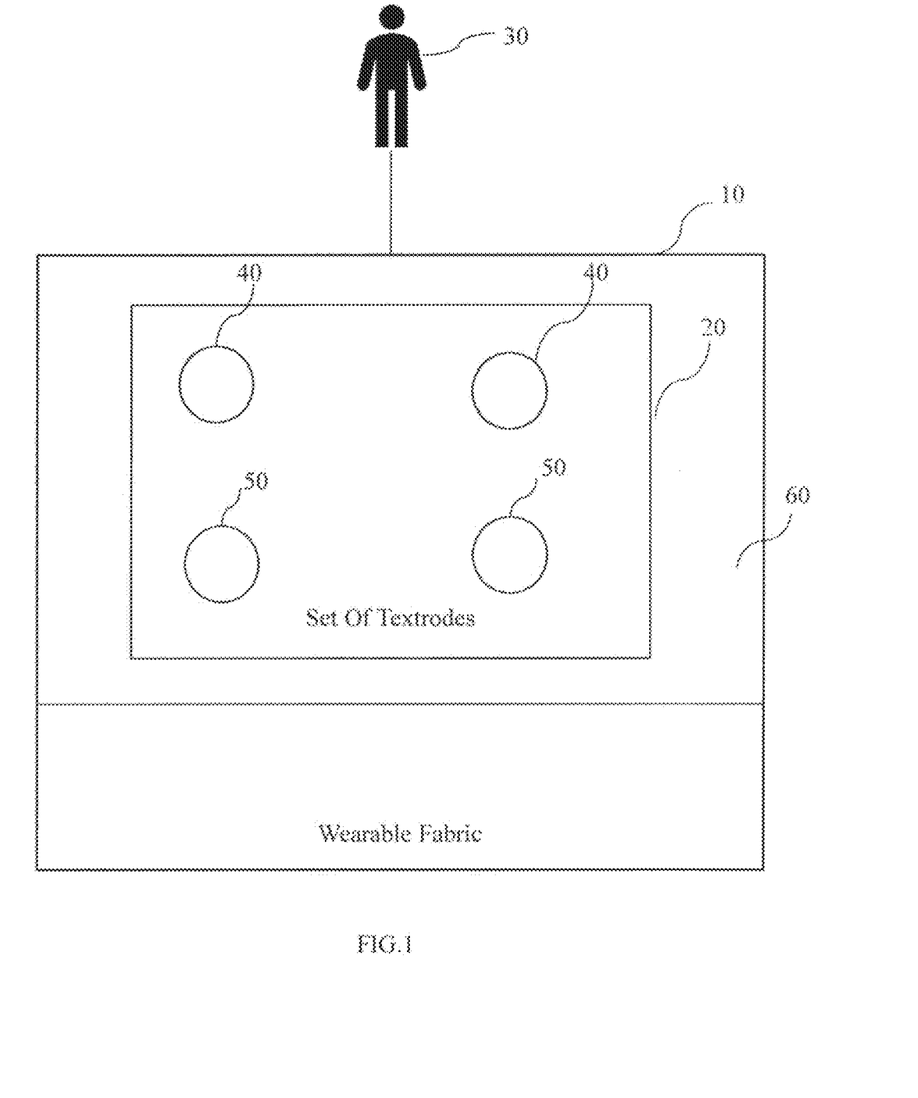
FIG. 1 is a block diagram representation of u wearable health monitoring fabric in accordance with an embodiment of the present disclosure.

FIG. 1 is a block diagram representation of a wearable health monitoring fabric in accordance with an embodiment of the present disclosure. The wearable fabric 10 includes a set of textrodes 20. As used herein, the wearable fabric 10 which is also referred as electronic textile, a smart garment, a smart clothing, a smart textile, or a smart fabric is defined as a type of fabric which enables one or more electrical and electronic components to be embedded into the fabric. In one specific embodiment, the wearable fabric 10 may be composed of a polyester Lycra fabric. In another embodiment, the set of textrodes may be composed of a material consisting of conductive Shieldex®"P130+B", a 2D stretchable, synthetic wrap-knitted silver coated fabric. "P130+B" is made of 78% polyamide, and 22% elastomer, and coated with 99% conductive silver particles with a surface resistivity p<2 Ω/sq.

In another embodiment, the wearable fabric 10 may be designed including, but not limited to, as a vest, a shirt, a T-shirt, a jacket, a bra or a top. In another embodiment, the wearable fabric 10 may be designed as a functional garment which may be used for physiological sensing in several disciplines such as sports, fire-fighting, military and medicine. In such embodiment, the wearable fabric 10 is worn by a user on an upper part of a user's body 30. The upper part 60 of the user's body 30 may correspond to an upper limb of the user's body 30. The user 30 may be a person who may or may not require a continuous medical assistance.

Furthermore, as used herein, a text rode is defined as a type of electrode which is fabricated along with the fabric during manufacture. The structure of textile electrodes can be fabricated by weaving, knitting, or embroidering the conductive yarn. In such embodiments, the set of textrodes 20 embedded in the garment may be used to monitor vital signs and other physiological parameters of the user's body 30.

Furthermore, the set of textrodes 20 are configured to measure thoracic electrical bioimpedance (TEB) of the user's body 30. As used herein, the thoracic electrical bioimpedance (TEB) is defined as a measure blood flow through aorta that is detected by the changes in thoracic impedance (Z), pulmonary artery diastolic pressure (PAD), cardiac output (CO) and stroke volume (SV) of the user's body 30.

In one specific embodiment, the thoracic electrical bioimpedance may be measured by the set of textrodes 20 in real-time. In another embodiment, based on the thoracic electrical bioimpedance of the user 30, a level of accumulation of fluids in lungs of the user may be measured in terms of PAD and Z. In yet another embodiment, the measurements of PAD and Z may typically demonstrate an inverse correlation, particularly in the 14 and 30 days before a heart failure event. Importantly, Z may remain relatively constant until PAD crossed a particular threshold at which point, presumably, compensatory mechanisms to regulate lung fluid accumulation may be exhausted and Z began to fall. In such embodiment, these observations may highlight the primary role of increased cardiac filling pressures in the triggering episodes of acute decompensation of heart failure (ADHF) and suggest that multiple sensor strategies might be optimally employed by using a temporal sequence whereby hemodynamic or pressure-based sensors may be used for early monitoring or prevention and impedance-based sensors are used for early detection or treatment of the user. Moreover, the set of textrodes 20 may be operatively coupled to a foam layer which may be configured to make a contact with skin of the user's body 30, in order to adjust the textrode-skin impedance for optimal measurement of thoracic impedance.

Furthermore, the set of textrodes 20 includes at least two first textrodes 40. In one embodiment, the at least two first textrodes 40 may include a first voltage sensing textrode and a first current injecting textrode. In such embodiment, the first voltage sensing textrode may be a positive voltage sensing textrode. The first current injecting textrode may be a positive current injecting textrode.

In addition, the set of textrodes 20 also includes at least two second textrodes 50. In one embodiment, the at least two second textrodes 50 may include a second voltage sensing textrode and a second current injecting textrode. In such embodiment, the second voltage sensing textrode may be a negative voltage sensing textrode. The second current injecting textrode may be a negative current injecting text rode.

Furthermore, the set of textrodes 20 is lubricated on in tipper part 60 of the wearable fabric. In one embodiment, the upper part of the wearable fabric may correspond to a thoracic region of the user's body 30. As used herein, the thoracic region is defined as a region of a human body located between a neck and an abdomen region of the human body.

Furthermore, the set of textrodes 20 is fabricated on in upper part 60 of the wearable fabric. In one embodiment, the upper part of the wearable fabric may correspond to a thoracic region of the user's body 30. As used herein, the thoracic region is defined as a region of a human body located between a neck and an abdomen region of the human body.

In one exemplary embodiment, the positive current injecting textrode and the positive voltage sensing textrode may be fabricated on a back side of the upper part 60 of the wearable fabric 10. In such embodiment, the back side of the upper part 60 of the wearable fabric 10 may correspond to a rear neck region of the user's body 30. Further, the negative current injecting textrode and the negative voltage sensing textrode may be fabricated either on a lower right region or, on a lower left region of the lower part of the wearable fabric 10. In such embodiment, the lower right region may correspond to a right abdominal region of the user's body 30 and the lower left region may correspond to a left abdominal region of the user's body 30.

In another embodiment, the positive current injecting textrodes may be fabricated on the back side of the upper part 60 of the wearable fabric 10, the positive voltage sensing textrode may be fabricated on a from side of the upper part 60 of the wearable fabric 10. In such embodiment, the front side of the upper part 60 may correspond to a front neck region of the user's body 30. Further, the negative current injecting textrode may be fabricated at a lower back region of the lower part of the wearable fabric 10 and the negative voltage sensing textrode may be fabricated on a lower front region of the lower part of the wearable fabric 10. In such embodiment, the tower back region corresponds to a lower spinal region of the user's body 30 and the lower front region corresponds to a lower abdominal region of the user's body 30.

In another embodiment, the wearable fabric 10 may further include one or more sensors (not shown in FIG. 1) which may be operatively coupled to one or more textrodes. The one or more sensors may be configured to sense one or more physiological signals from the wearer's body 30. The one or more sensors may include a hemodynamic or, pressure sensor and a temperature sensor. The hemodynamic/pressure sensor may include at least one of an electrocardiogram sensor, an inertial sensor, a photoplethysmogram sensor, and a thoracic bioimpedance sensor, further, the one or more physiological signals which may be sensed by the corresponding one or more sensors may include a heart muscle's electrophysiologic pattern, an inertial state of the user, a photoplethysmogram measurement, a respiratory rate, an oxygen saturation level, a blood pressure, a skin temperature, a skin impedance and a thoracic impedance. In one embodiment, the one or more physiological signals may be associated to at least one of a cardiovascular disease (CVD), a chronic obstructive pulmonary disease (COPD), a type 2 diabetes (T2D) and associated trauma disease of the wearer.

In one further embodiment, the wearable fabric 10 may further include a computing device operatively coupled to the wearable fabric 10. The computing device is configured to obtain and process the one or more health signals sensed by the corresponding one or more sensors.

In another embodiment, more sophisticated sensor technologies may be included that are capable of detecting very early pathophysiologic changes and using them to target upstream therapy. One such embodiment may include the one or more textrodes that might significantly alter different biomarkers in both acute and chronic HF including blood chemistries such as electrolytes, glucose and pH, natriuretic peptides (i.e., B-type natriuretic peptide [BNP], N-terminal proBNP, atrial natriuretic peptide), inflammatory makers (i.e., tumor necrosis factor-$\alpha$, interleukin-6, interleukin-1), oxidative stress markers (i.e., myeloperoxidase), and collagen turnover/extracellular matrix peptides (i.e., C-terminal propeptide of collagen type 1, matrix metalloproteinase, tissue inhibitor of matrix metalloproteinases). Additionally, using metabolomic technologies, novel pathways are being implicated in the pathophysiology of HF and may identify markers that are capable of detecting even more subtle alterations in CHF such as changes in myocardial signaling and energetics.

In yet another embodiment, the wearable fabric 10 may further include a computing device (not shown in FIG. 1) which may be operatively coupled to the wearable fabric 10. The computing device may be configured to obtain and process a measured thoracic electrical bioimpedance (TEB) in order to monitor the fluid accumulation in lungs of the wearer in real-time. In another embodiment, the computing device may also be configured to obtain and process a sensed one or more signal which may be generated by the corresponding one or more sensors. In one specific embodiment, based on a processed inertial slate of the user 30, a condition may be determined to know whether the user is awake or asleep.

Figure 2:
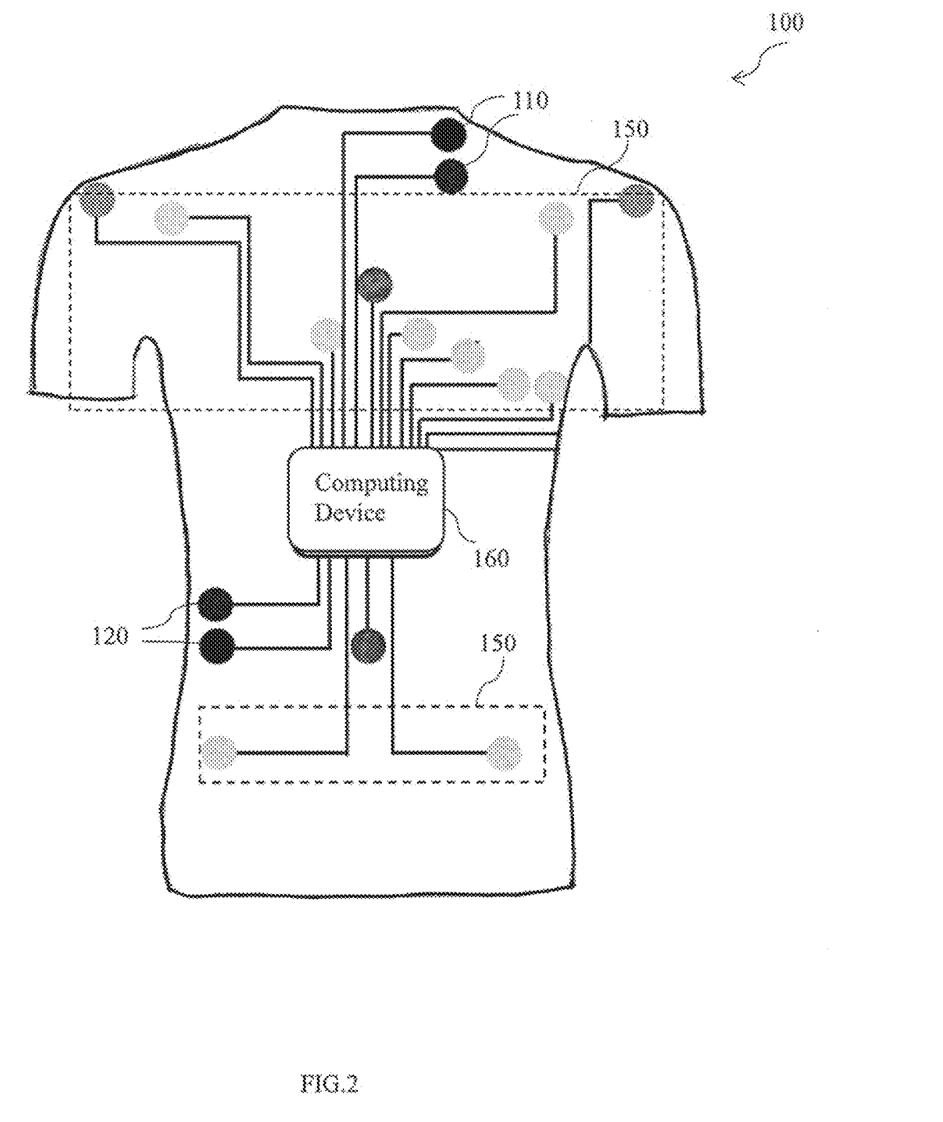
FIG. 2 is a schematic representation of a wearable health monitoring fabric of FIG. 1 in accordance with an embodiment of the present disclosure.

FIG. 2 is a schematic representation of a wearable health monitoring fabric of FIG. 1 in accordance with an embodiment of the present disclosure. A wearable fabric 100 includes two first textrodes 110 and two second textrodes 120. Furthermore, the two first textrodes 110 includes the positive voltage sensing textrode and the positive current injecting textrode which are fabricated on the upper region of the wearable fabric 100. The two second textrodes 120 includes the negative voltage sensing textrode and the negative current injecting textrode are fabricated at the lower right region of the wearable fabric 100. More specifically, the two first textrodes 110 are fabricated on a top left portion of the upper part of the wearable fabric 100 and the two second textrodes 120 are fabricated on a bottom right portion of the wearable fabric 100 on the thoracic region of a user's body. Further, the two first textrodes 110 and two second textrodes 120 are configured to measure thoracic electrical bioimpedance (TEB) of the patient.

Furthermore, the wearable fabric 100 is operatively coupled with the plurality of sensors 150 which are operatively coupled to one or more textrodes (not shown). The plurality of sensors 150 are configured to measure the corresponding plurality of physiological parameters. The plurality of sensors 150 may include a ten lead ECG sensor configured to determine the heart muscle's electrophysiologic pattern a two lead accelerometer or, inertia sensor configured to determine the physical state of the wearer (if the wearer is awake or, in sleep), a one lead chest photoplethysmography sensor configured to determine the oxygen saturation level of the heart muscles and a two lead skin temperature sensors embedded in the accelerometer or, inertia sensor. Also, the wearable fabric 100 is operatively coupled with the computing device 160 and configured to obtain and process the thoracic electrical bioimpedance and the plurality of physiological parameters obtained from the user. In one specific embodiment, the two first textrodes 110 and the two second textrodes 120 may include two voltage polarities and two current polarities and hence may be form a tetrapolar configuration. More specifically, the positive voltage sensing textrode, the negative voltage sensing textrode, the positive current injecting textrode and the negative current injecting textrode may together form a tetra polar configuration. Further, in one embodiment, the two first textrodes 110 and the two second textrodes 120 may be placed lateral spot electrode configuration. In another embodiment, the two first textrodes 110 and the two second textrodes 120 may be placed in a whole body approach.

Further, an alternating current with a frequency between 50 Hz up to 100 kHz may be injected to obtain the differential voltage in the experimental range of operation for the thoracic impedance measurement. Also, to facilitate an electrical connection between the first textrodes 110, the second textrodes 120 and the computing device 160, a conducive male snap button may be used.

In one preferred embodiment, polarity of the positive voltage sensing textrode and the negative voltage sensing textrode may be interchanged. Similarly, the polarity of the positive current injecting textrode und the positive current injecting textrode may be interchanged.

Furthermore, the two first textrodes 110 and the two second textrodes 120 are substantially similar to at least two first textrodes 40 and the at least two second textrode 50 of FIG. 1.

Figure 3:
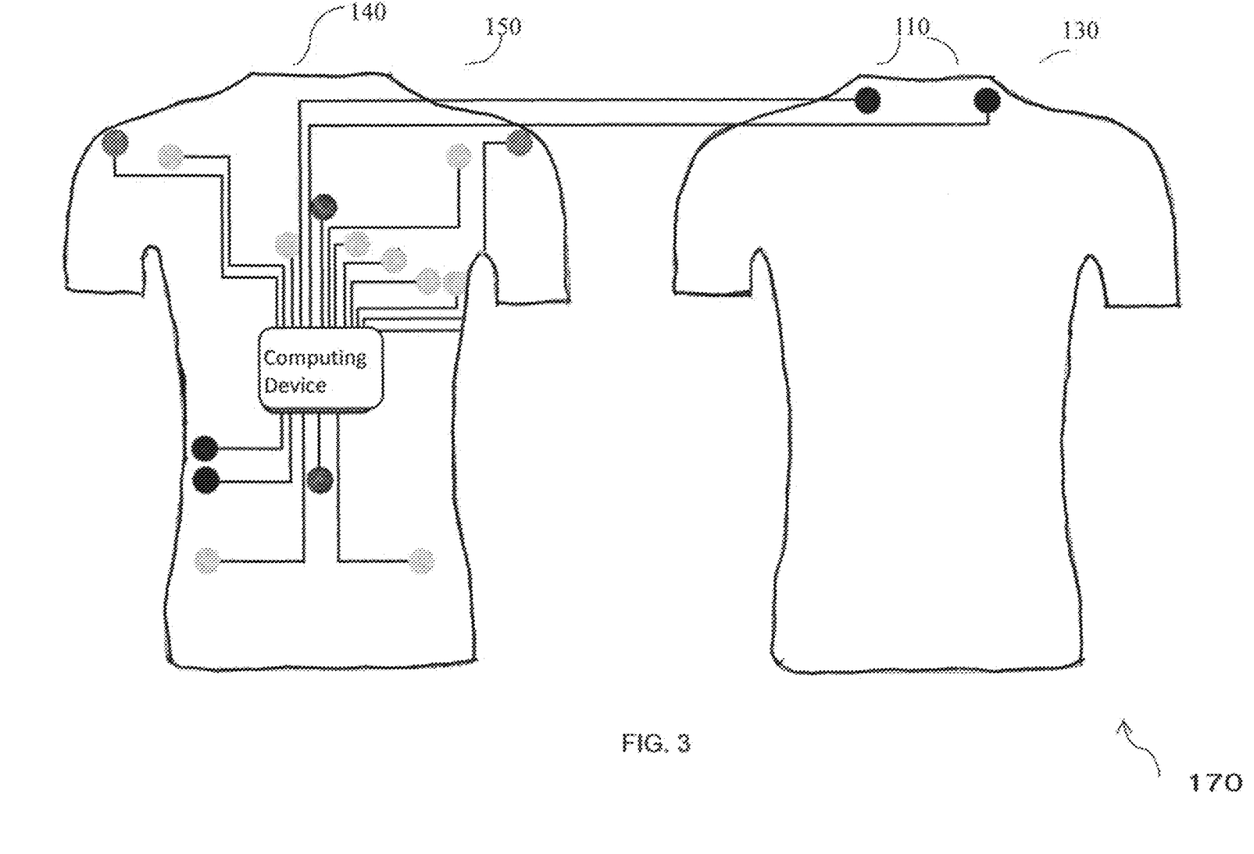
FIG. 3 is a schematic representation of an exemplary embodiment of a wearable vest to determine a patient's health of FIG. 1 in accordance with an embodiment of the present disclosure.

FIG. 3 is a schematic representation of an exemplary embodiment of a wearable vest to determine a patient's health of FIG. 1 in accordance with an embodiment of the present disclosure. Any person (not shown in FIG. 3) who is in need of a continuous real-time health monitoring is referred to wear the wearable vest 170 for continuous assistance of the patient. The positive voltage sensing textrode and the positive current injecting textrode of the two first textrodes 110 are fabricated on an upper back region 130 of a wearable vest 170, wherein the wearable vest 170 is substantially similar to a wearable fabric 10 of FIG. 1 and wearable fabric 100 of FIG. 2. Further, the negative voltage sensing textrode and the negative current injecting textrode are fabricated at the lower right region of a front part 140 of the wearable vest 170. Further, the upper buck region 130 and the lower right region of a from pan 140 are located within the thoracic region of the patient's body.

Furthermore, the wearable vest 170 is operatively coupled to the plurality of sensors 150 and the computing device 160 which are configured to measure and process the plurality of health parameters which is obtained from the patient.

Figure 4:
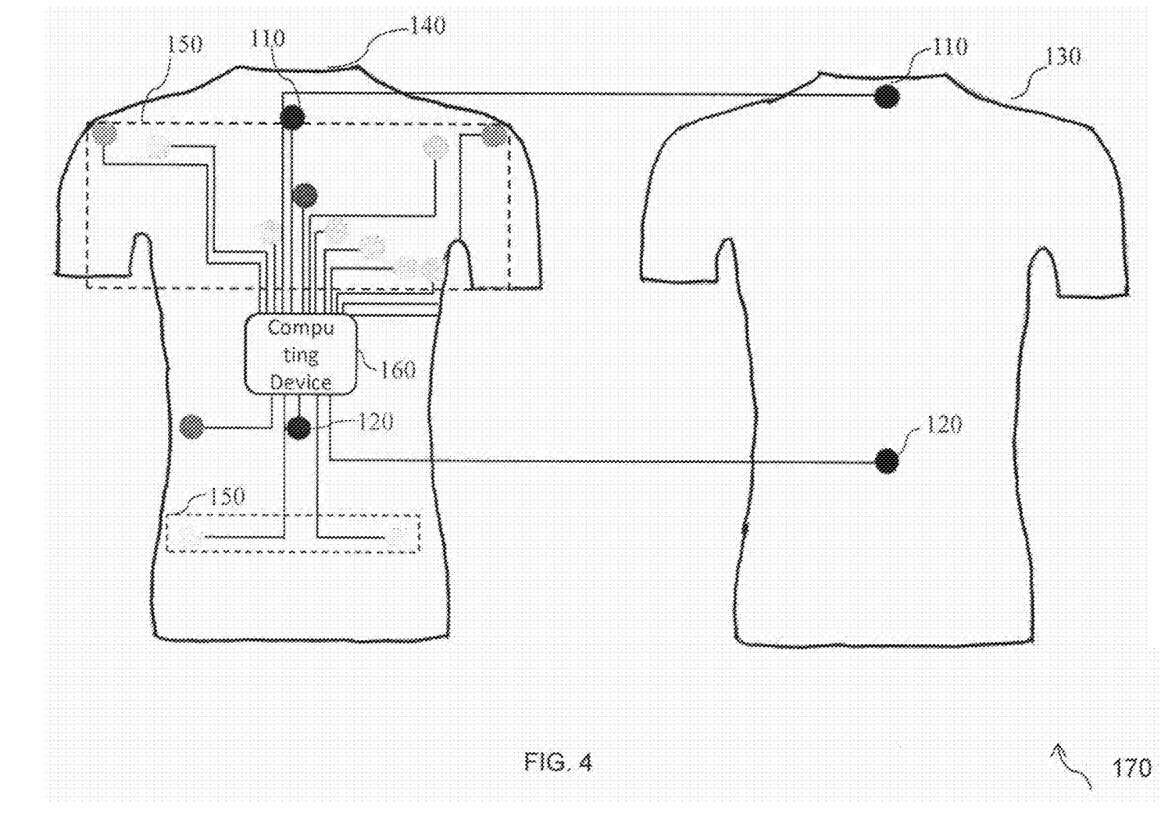
FIG. 4 is a schematic representation of another exemplary embodiment of the wearable vest to determine the patient's health of FIG. 1 in accordance with an embodiment of the present disclosure.

FIG. 4 is a schematic representation of another exemplary embodiment of the wearable vest to determine the patient's health of FIG. 1 in accordance with an embodiment of the present disclosure. The positive voltage sensing textrode of the two first textrodes 110 is fabricated on the upper region of the front side 140 of a wearable vest 170, wherein the wearable vest 170 is substantially similar to the wearable fabric 10 of FIG. 1 and the wearable fabric 100 of FIG. 2 Further, the positive current injecting textrode of the two first textrodes 110 is fabricated on the upper region of the back side 130 of the wearable vest 170.

Furthermore, the negative voltage sensing textrode of the second textrode 120 is fabricated on a mid-region of the lower part of the front side 140 and the negative current injecting textrode of the second textrode 120 is fabricated on the mid-region of the lower part of the hack side 130 of the wearable vest 170.

The upper region of the front side 140, the upper region of the back side 130, the mid-region of the lower part of the front side 140 and the mid-region of the lower part of the back side 130 are located within the thoracic region of the patient's body.

Figure 5:
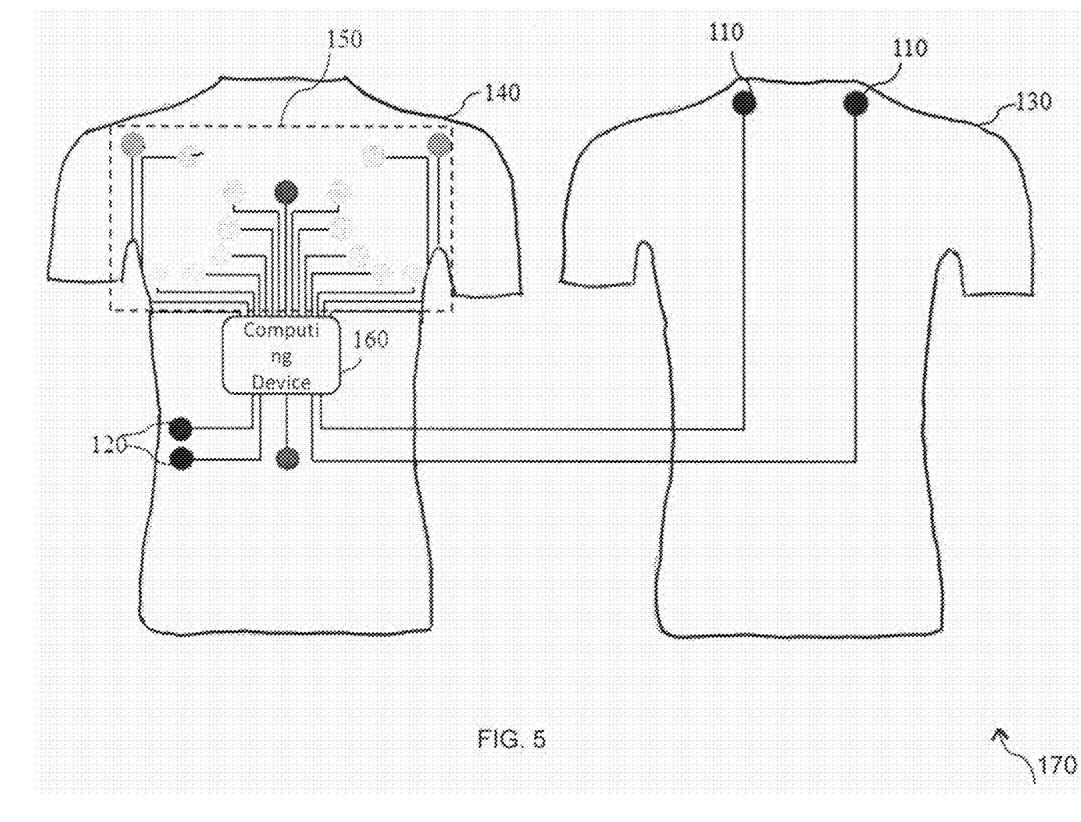
FIG. 5 is a schematic representation of yet another exemplary embodiment of the wearable vest to determine the patient's health of FIG. 1 in accordance with an embodiment of the present disclosure.

FIG. 5 is a schematic representation of yet another exemplary embodiment of the wearable vest to determine the patient's health of FIG. 1 in accordance with an embodiment of the present disclosure. The two first textrodes 110 includes a positive voltage sensing textrode and a positive current injecting textrode which are fabricated on an upper back region 130 of the wearable vest 170. The two second textrodes 120 includes a negative voltage sensing textrode and a negative current injecting textrode which are fabricated at a lower right region of the front pan 140 of the wearable vest 170. Further, the two first textrodes 110 and two second textrodes 120 are configured to measure thoracic electrical bioimpedance (TEB) of the patient. Further, the upper back region 130 and the lower right region of the front part 140 are located within the thoracic region of the patient's body.

In addition, the wearable vest 170 is fabricated with a plurality of sensors 150 which are operatively coupled to the one or more textrodes configured to measure a corresponding plurality of health parameters.

Figure 6:
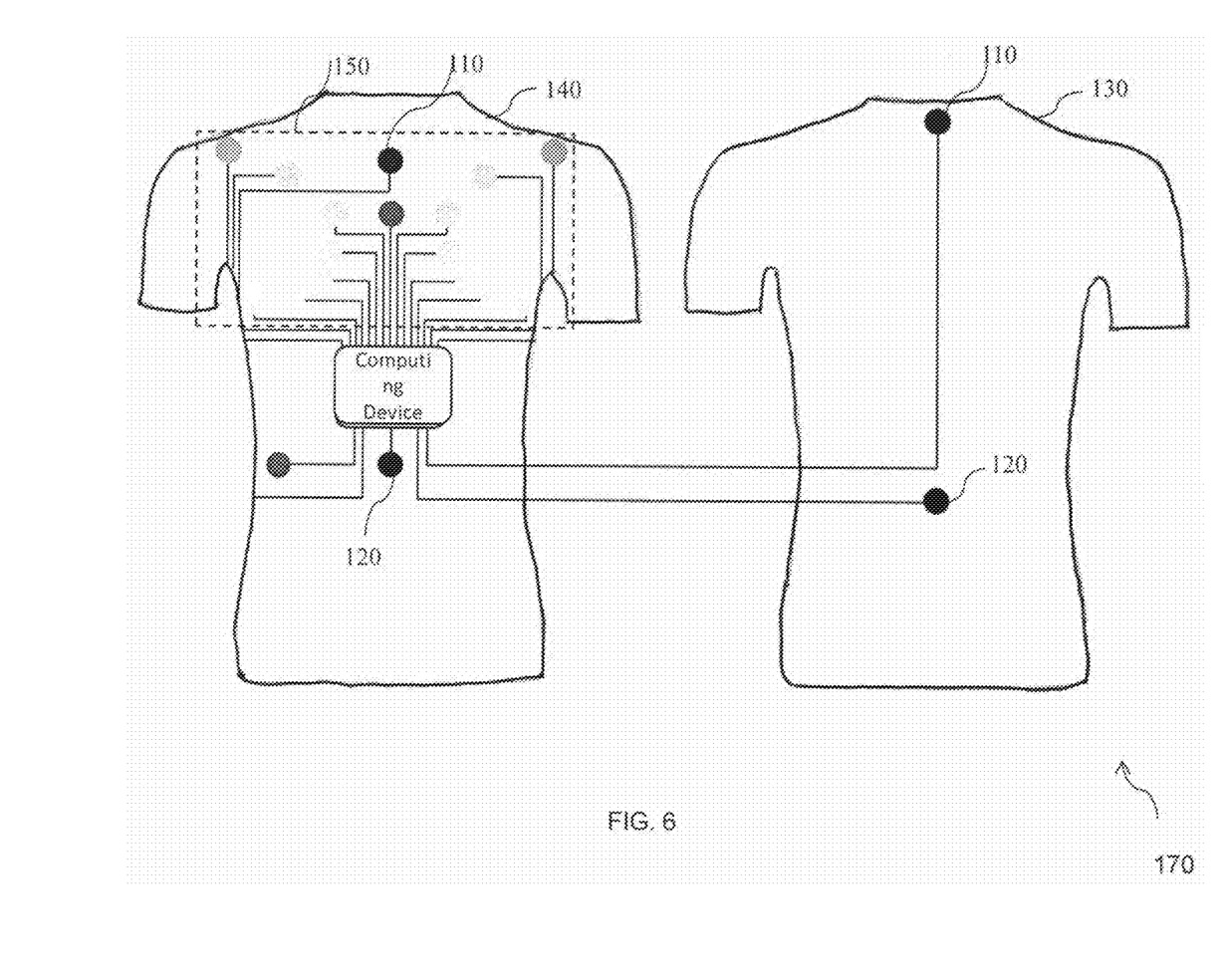
FIG. 6 is a schematic representation of yet another exemplary embodiment of the wearable vest to determine the patient's health of FIG. 1 in accordance with an embodiment of the present disclosure.

FIG. 6 is a schematic representation of yet another exemplary embodiment of the wearable vest to determine the patient's health of FIG. 1 in accordance with an embodiment of the present disclosure. The positive voltage sensing textrode of the two first textrodes 110 is fabricated on the upper region of the front side 140 of a wearable vest 170, wherein the wearable vest 170 is substantially similar to the wearable fabric 10 of FIG. 1 and the wearable vest 100 of FIG. 2. Further, the positive current injecting textrode of the two first textrodes 110 is fabricated on the upper region of the back side 130 of the wearable vest 170.

Furthermore, the negative voltage sensing textrode of the second textrode 120 is fabricated on a mid-region of the lower part of the front side 140 and the negative current injecting textrode of the second textrode 120 is fabricated on the mid-region of the lower part of the back side 130 of the wearable vest 170. Further, the plurality of sensors 150 includes a twelve lead ECG sensor configured to determine the heart muscle's electrophysiologic pattern. The plurality of sensors 150 is also configured to measure the health parameters of the patient.

Further, the upper region of the front side 140, the upper region of the back side 130, the mid-region of the lower part of the front side 140 and the mid-region of the lower part of the back side 130 are located within the thoracic region of the patient's body.

Figure 7:
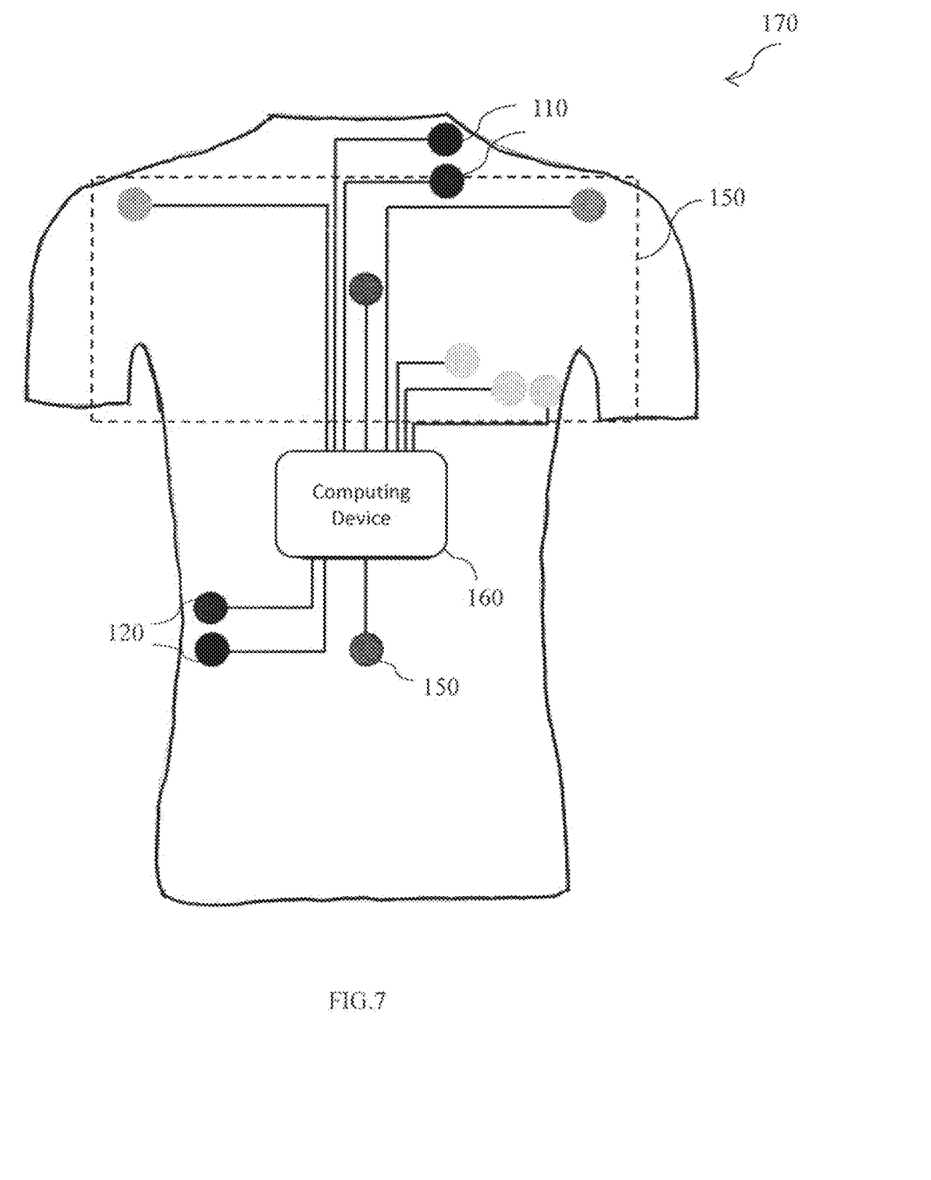
FIG. 7 is a schematic representation of yet another exemplary embodiment of the wearable vest to determine the patient's health of FIG. 1 in accordance with an embodiment of the present disclosure.

FIG. 7 is a schematic representation of yet another exemplary embodiment of the wearable vest to determine the patient's health of FIG. 1 in accordance with an embodiment of the present disclosure. The two first textrodes 110 are fabricated on the upper left region of the wearable vest 170 and the two second textrodes 120 are fabricated on the lower right region of the wearable west 170. Further, the plurality of sensors may include a three-lead EGG sensors positioned in V3, V4 and V5 configurations, the IMU sensors and the PPG sensors operatively coupled to the one or more textrodes, wherein the one or more textrodes are fabricated within the wearable vest 170. Further, the upper left region and the lower right region are located within the thoracic region of the patient's body.

Further, the plurality of sensors 150 are operatively coupled to the computing device 160, and configured to measure the health parameters of the patient.

Figure 8:
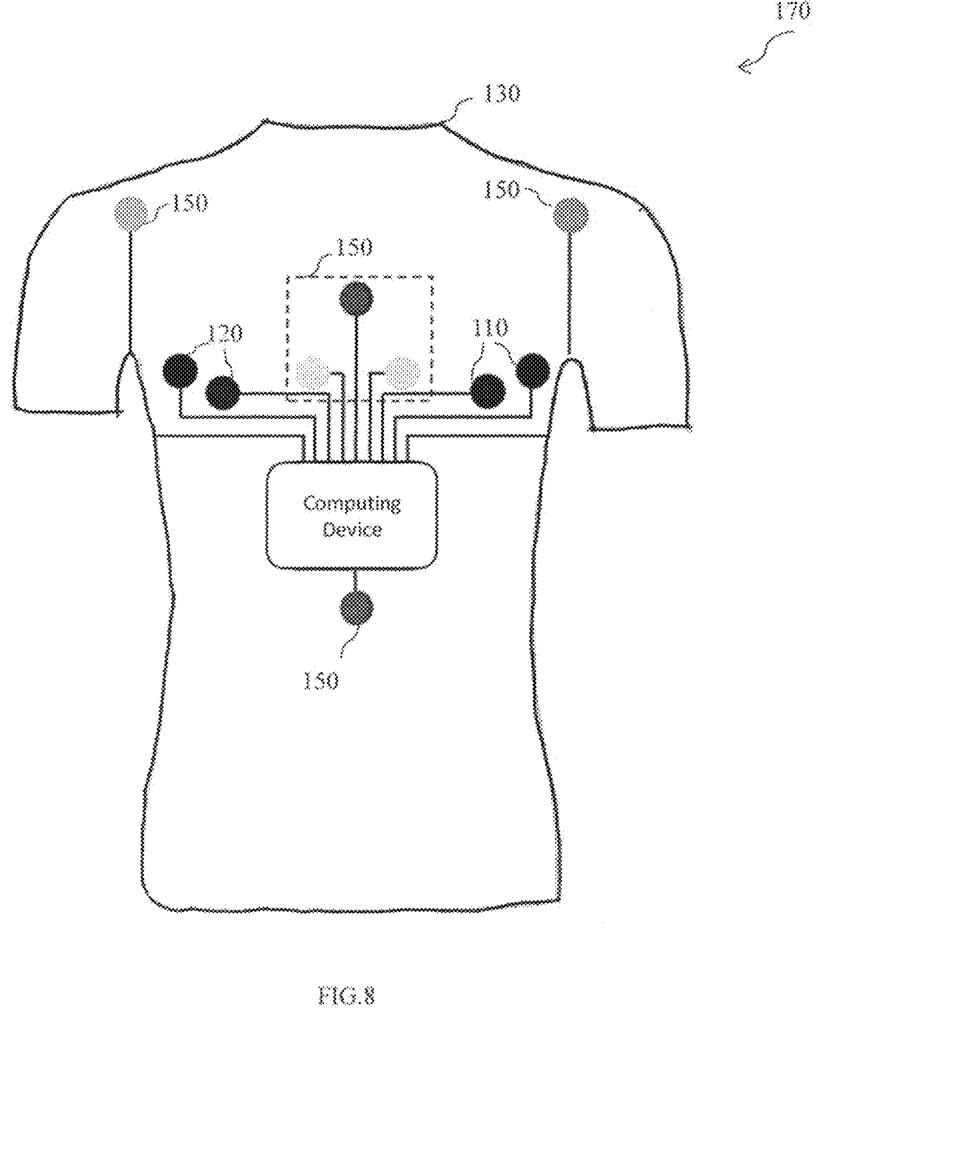
FIG. 8 is a schematic representation of yet another exemplary embodiment of the wearable vest to determine the patient's health of FIG. 1 in accordance with an embodiment of the present disclosure.

FIG. 8 is a schematic representation of yet another exemplary embodiment of the wearable veil to determine the patient's health of FIG. 1 in accordance with an embodiment of the present disclosure. The two first textrodes 110 and the two second textrodes 120 are fabricated on a lower right region and a lower left region of the upper part on the front side 130 of a wearable vest 170 respectively. The wearable vest 170 is substantially to a wearable fabric 10 of FIG. 1. Further the plurality of sensors 150 includes a single lead ECG sensor and the chest photoplethysmogram censor to determine the heart muscle's electrophysiologic pattern and the oxygen saturation level of the patient.

Figure 9:
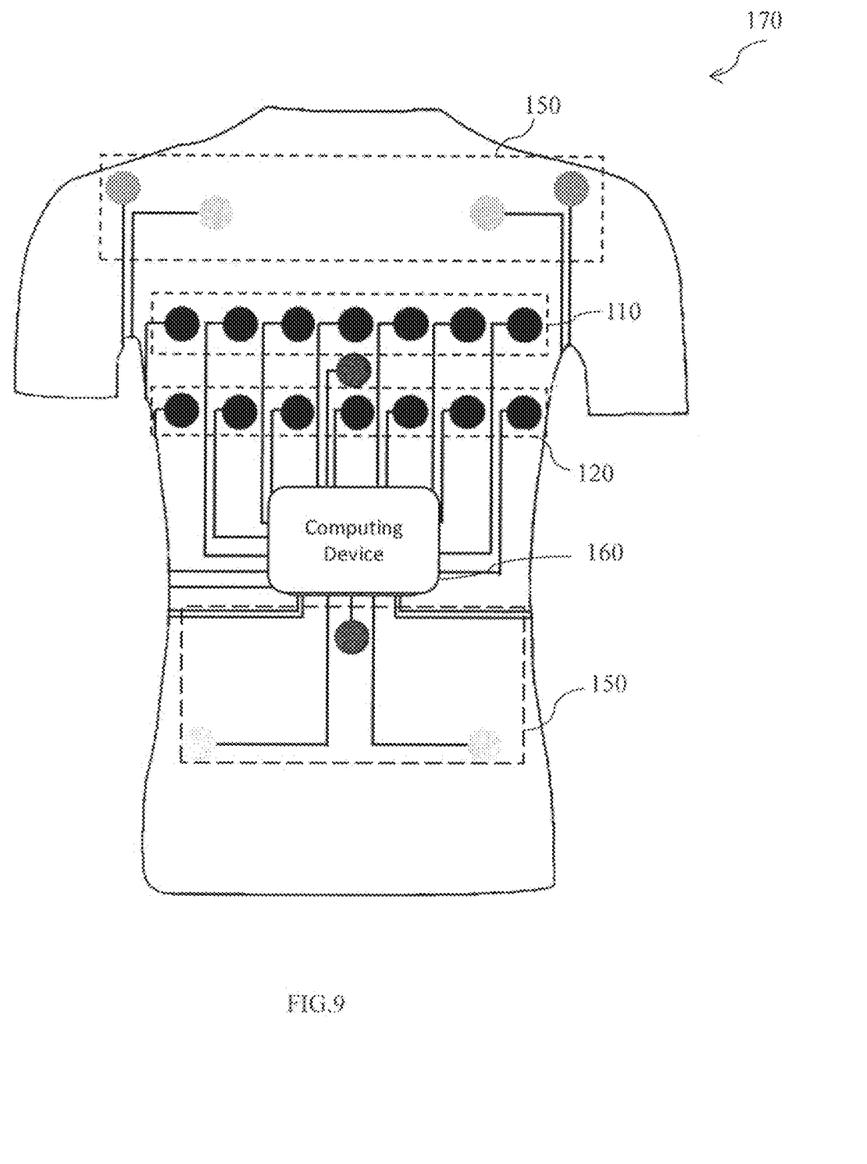
FIG. 9 is a schematic representation of yet another exemplary embodiment of the wearable vest to determine the patients health of FIG. 1 in accordance with an embodiment of the present disclosure.

FIG. 9 is a schematic representation of yet another exemplary embodiment of the wearable vest to determine the patient's health of FIG. 1 in accordance with an embodiment of the present disclosure. At least two first textrodes of the wearable vest 170 includes a plurality of first textrodes 110. Further, the plurality of first textrodes 110 includes a plurality of positive voltage sensing textrodes and a plurality of positive current injecting textrodes. At least two second textrodes includes a plurality of second textrodes 120. The plurality of second textrodes 120 includes a plurality of negative voltage sensing textrodes and a plurality of negative current injecting textrodes. Further, the plurality of first textrodes 110 and the plurality of second textrodes 120 are fabricated on the thoracic region of the patient, and is configured to measure thoracic electrical bioimpedance (TEB) of the patient.

Furthermore, the plurality of sensors 150 are 150 are operatively coupled to the computing device 160, and configured to measure the health parameters of the patient.

Further the plurality of first textrodes 110 and the plurality of second textrodes 120 can be switched between a current injecting and a voltage measurement function. Each of the active textrode mas contains an electronic buffer to pre-process the measured voltages. Further, voltage measurement circuit, the current source circuit and the skin contact impedance measurements circuits are located within the computing device. Consequently, the plurality of first textrodes 110 and the plurality of second textrodes 120 may be used for real time monitoring of lungs & heart for moving real time image of the patient.

Furthermore, skin contact impedances are measured at the positive current injecting textrode and the negative current injecting textrode. The measured skin contact impedance includes the junction between the two first textrodes 110 and the two second textrodes 120 and skin, the skin impedance and part of the body tissue between the two positive injecting textrode and the negative current injecting textrode. In a specific embodiment, the wearable vest 170 [may include of a striped conductive textile cover and a 3D spacer fabric wrapped around a core made of a flexible PCB carrying 2n active textrodes (n=any integer). On average, two adjacent conductive stripes, separated by non-conductive polyester fabric are in electrical contact with the textrodes. This set-up may be used for real time monitoring of lungs & heart for moving real time images in the clinical setting: highly stable electrical contact between electrode and skin, placement of textrodes at anatomically predefined and known positions, easy and quick but highly reproducible application of the textrodes in the clinical setting, skin friendly breathable vest design, to allow continuous real time monitoring and non-ionic and non-conducting agent enhancing the electrical contact between the textrodes and the skin while catering for the needs of the latter.

Various embodiments of the wearable health monitoring fabric enable the wearable fabric to implement a non-invasive type of electrode to measure the health parameters of the user. Hence making the wearable fabric more compatible, user friendly and cost-effective. Also, the wearable device docs not require any type of adhesive to fasten the textrodes to the user's body.

In addition, the textrodes used in the wearable fabric provide accurate measurements of the physiological parameters which makes the wearable fabric smart and efficient. Furthermore, the wearable fabric material acts as an insulator to the user's body and hence protects the user from unnecessary electrical signals which may be generated by one or more electronic components fabricated within the wearable fabric.

While specific language has been used to describe the disclosure, any limitations arising on account of the same are not intended. As would be apparent to a person skilled in the art, various working modifications may be mode to the method in order to implement the inventive concept as taught herein.

The figures and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, order of processes described herein may be changed and are not limited to the manner described herein. Moreover, the actions of any flow diagram need not be implemented in the order shown; nor do all of the acts need to be necessarily performed. Also, those acts that are not dependent on other acts may be performed in parallel with the other acts. The scope of embodiments is by no means limited by these specific examples.

We claim:

1. A wearable fabric to monitor a user's health, comprising:
a set of textrodes, configured to sense one or more physiological signals generated by the user's body including measuring Thoracic Electrical Bioimpedance (TEB) of the user's body, comprises:
at least two first textrodes;
at least two second textrodes;
wherein the set of textrodes is fabricated on an upper part of the wearable fabric, and
wherein the at least two first textrodes comprise a first voltage sensing textdrode and a first current injecting textrode and the at least two second textrodes comprise a second voltage sensing textrode and second current injecting textrode; and
one or more sensors woven in the wearable fabric and configured to capture electrocardiogram (ECG) of the user, wherein the one or more sensors comprise a twelve lead ECG configured to identify markers for detecting myocardial signalling and energetics.

2. The wearable fabric as claimed in claim 1, wherein the wearable fabric is designed as a vest, a shirt, a T-Shirt, a jacket, or a top.

3. The wearable fabric as claimed in claim 1, wherein the set of textrodes comprises at least one of a textile electrodes, woven electrodes and an embroidered textile electrode.

4. The wearable fabric as claimed in claim 1, wherein the upper part of the wearable fabric corresponds to a thoracic region of the user's body.

5. The wearable fabric as claimed in claim 1, wherein the one or more sensors further comprise a hemodynamic sensor, wherein the hemodynamic sensors comprise at least one of an electrocardiogram sensor, an inertia sensor, a photoplethysmogram sensor, a temperature sensor and a thoracic impedance.

6. The wearable fabric as claimed in claim 1, wherein the one or more physiological signals further comprises at least one of a heart muscle's electrophysiologic pattern, a respiratory rate, an oxygen saturation level, a blood pressure, a skin temperature, and a skin impedance.

7. The wearable fabric as claimed in claim 1, further comprising a computing device operatively coupled to the wearable fabric, and configured to obtain and process the one or more physiological signals sensed by the set of textrodes.

8. The wearable fabric as claimed in claim 1, further comprising a computing device operatively coupled to the wearable fabric and configured to obtain and process a measured thoracic electrical bioimpedance (TEB).

* * * * *